United States Patent [19]

Peet et al.

[11] Patent Number: 4,487,930
[45] Date of Patent: Dec. 11, 1984

[54] 6-[(CYCLIC AMINO)ALKYLAMINO]-TETRAHYDRO-TRIAZOLO[3,4-A]PHTHALAZINES

[75] Inventors: Norton P. Peet; Catherine A. Alexander, both of Indianapolis, Ind.

[73] Assignee: The Dow Chemical Company, Midland, Mich.

[21] Appl. No.: 414,766

[22] Filed: Sep. 7, 1982

[51] Int. Cl.[3] .................... C07D 487/04; A61K 31/50
[52] U.S. Cl. .................................... 544/234; 424/250
[58] Field of Search .............. 544/236, 234, 115; 424/250

[56] References Cited

U.S. PATENT DOCUMENTS

| 2,484,629 | 10/1949 | Hartmann et al. | 424/250 |
| 3,079,392 | 2/1963 | Pesson | 544/234 |
| 3,096,329 | 7/1963 | Steck | 424/250 |
| 3,483,193 | 12/1969 | Gall et al. | 424/250 |
| 3,708,848 | 1/1973 | Anderson et al. | 424/250 |
| 3,915,968 | 10/1975 | Bellasio et al. | 424/250 |
| 4,016,162 | 4/1977 | Bellasio et al. | 424/250 |
| 4,112,095 | 9/1978 | Allen et al. | 544/239 |
| 4,136,182 | 1/1979 | Lewis et al. | 424/250 |
| 4,272,535 | 6/1981 | Blythin et al. | 544/115 |

FOREIGN PATENT DOCUMENTS

| 883836 | 10/1971 | Canada | 548/262 |
| 2741763 | 3/1978 | Fed. Rep. of Germany | 424/250 |
| 1248409 | 11/1960 | France | 544/234 |
| 3021197 | 8/1976 | Japan | 544/234 |
| 2061275 | 5/1981 | United Kingdom | 424/250 |

OTHER PUBLICATIONS

Lundina, et al., *Chem. Abst.* 67, 21884q, (1967).
Davies, et al., "n. Anti-Bronchoconstrictor . . . ", *Nature New Biology* 234, 50, (1971).
Basu, et al., "s-Triazolopyrimidines . . . ", *J. Chem. Soc.*, 1963, 5660.
Pollack, et al., ". . . Pyridazine Derivatives," *Tetrahedron*, 22, 2073-2079, (1966).
Noller, Carl, *Textbook of Organic Chemistry*, W. B. Saunders, Philadelphia, (1966), p. 422.

*Primary Examiner*—Nicholas S. Rizzo
*Assistant Examiner*—G. Hendricks
*Attorney, Agent, or Firm*—John W. Kolano; Gary D. Street; Richard G. Waterman

[57] ABSTRACT

6-[(Cyclic amino)alkylamino]-7,8,9,10-tetrahydro-1,2,4-triazolo[3,4-a]phthalazines are novel compounds prepared by the reaction of a 6-halo-7,8,9,10-tetrahydro-1,2,4-triazolo[3,4-a]phthalazine with an appropriate (cyclic amino)alkylamine. The compounds are useful as bronchodilators.

5 Claims, No Drawings

6-[(CYCLIC AMINO)ALKYLAMINO]-TETRAHYDRO-TRIAZOLO[3,4-A]PHTHALAZINES

The present invention relates to tetrahydrotriazolo[3,4-a]phthalazines having a (cyclic amino)alkylamino substituent at the 6-position. More particularly, it relates to compounds having the following general formula

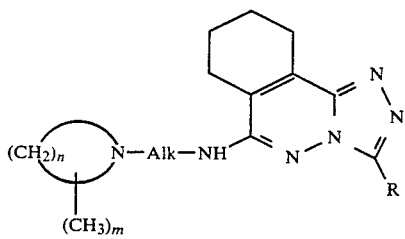

wherein R is hydrogen or lower alkyl of 1–4 carbon atoms; Alk is alkylene of 2–4 carbon atoms; m is 0 or 1; and n is 4 or 5; and the pharmaceutically acceptable acid addition salts thereof.

The lower alkyl group referred to above can be exemplified by groups such as methyl, ethyl, propyl and butyl. The alkylene groups referred to above separate the nitrogens attached thereto by at least two carbon atoms and can be exemplified by ethylene, propylene, trimethylene or tetramethylene. With the choices for m and n set forth above, the cyclic amino group contains only carbon and one nitrogen and the cyclic amines involved are 1-pyrrolidinyl or 1-piperidinyl, both optionally substituted with a methyl group.

Preferred compounds of the present invention are those wherein Alk is ethylene. A further preferred embodiment are those compounds wherein Alk is ethylene and R is hydrogen.

Acid addition salts of the amines of the present invention with pharmaceutically acceptable acids are equivalent to the amines for the purposes of this invention. Illustrative of such salts are the salts with inorganic acids such as, for example, hydrochloric, hydrobromic, sulfuric, phosphoric and like acids; with organic carboxylic acids such as, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxybenzoic, mandelic and like acids; and with organic sulfonic acids such as methanesulfonic acid and p-toluenesulfonic acid.

Examples of compounds encompassed by the present invention are the following:

6-[2-(1-Pyrrolidinyl)ethylamino]-7,8,9,10-tetrahydro-1,2,4-triazolo[3,4-a]phthalazine.

6-[2-(3-Methyl-1-pyrrolidinyl)ethylamino]-7,8,9,10-tetrahydro-1,2,4-triazolo[3,4-a]phthalazine.

3-Methyl-6-[2-(1-piperidinyl)ethylamino]-7,8,9,10-tetrahydro-1,2,4-triazolo[3,4-a]phthalazine.

6-[3-(2-Methyl-1-pyrrolidinyl)propylamino]-7,8,9,10-tetrahydro-1,2,4-triazolo[3,4-a]phthalazine.

6-[3-(1-Piperidinyl)propylamino]-7,8,9,10-tetrahydro-1,2,4-triazolo[3,4-a]phthalazine.

3-Methyl-6-[3-(1-pyrrolidinyl)propylamino]-7,8,9,10-tetrahydro-1,2,4-triazolo[3,4-a]phthalazine.

The substituted tetrahydrotriazolo[3,4-a]phthalazine compounds as described above are bronchodilators and are thus useful for the treatment of bronchial disorders such as bronchial asthma. The present invention is further directed to a method of effecting bronchodilation.

In practicing the method of this invention, an effective bronchodilating amount of 1 or more substituted tetrahydrotriazolo[3,4-a]phthalazines of this invention is administered internally to a mammal in need thereof by a route effective to bring the compound into contact with the bronchial and tracheal tissues of the mammal. Administration can be carried out either by a parenteral route, such as by intravenous, intraperitoneal or intramuscular injection, or by introduction into the gastrointestinal tract via oral or rectal administration, for example, in order to bring about such contact via the blood stream, or by intratracheal administration, by inhalation of a solution in the form of a spray or by inhalation of an aerosol formulation.

The effective bronchodilating amount of the compound, that is, the amount sufficient to inhibit or alleviate bronchial spasm, depends on various factors such as the size, type and age of the animal to be treated, the particular compound or pharmacologically-acceptable salt employed, the route and frequency of administration, the severity of any spasm and the causative agent involved, and the time of administration. In particular cases, the dosage to be administered can be ascertained by conventional range finding techniques, for example, by observing the bronchodilator activity produced at different dosage rates. More specifically, the compounds can be administered at dosage rates ranging from about 1 to about 200 milligrams of substituted tetrahydrotriazolo[3,4-a]phthalazine compound per kilogram of animal body weight with other ranges being from about 1 to about 100 or from 1 to about 50 milligrams per kilogram. It is generally desirable to administer individual dosages at the lowest amount which provides the desired protection from bronchial spasm consonant with a convenient dosing schedule. Dosage units adaptable to oral administration such as tablets, capsules, lozenges, elixirs, syrups and the like are generally preferred and the active compound can be formulated in conventional time release capsule or tablet formulations although injectable compositions or sprays and aerosols for inhalation are preferred when rapid action is desired.

In practicing the method of this invention, the active ingredient is preferably incorporated in a composition comprising a pharmaceutical carrier and from about 5 to about 90 percent by weight of the substituted tetrahydrotriazolo[3,4-a]phthalazine compound or a pharmaceutically-acceptable salt thereof. The term "pharmaceutical carrier" refers to known pharmaceutical excipients useful in formulating pharmaceutically active compounds for internal administration to animals, and which are substantially non-toxic and non-sensitizing under conditions of use. The compositions can be prepared by known techniques for the preparation of tablets, capsules, lozenges, troches, suppositories, elixirs, syrups, emulsions, dispersions, wettable and effervescent powders, sterile injectable compositions and solutions for sprays, and can contain suitable excipients known to be useful in the preparation of the particular type of composition desired. Suitable pharmaceutical carriers and formulation techniques are found in standard texts, such as Remington's Pharmaceutical Sciences, Mack Publishing Company, Easton, Pa.

In evaluating bronchodilator activity, test compounds were administered to guinea pigs either orally or by intraperitoneal injection and the guinea pigs were challenged by exposure to a histamine aerosol, generally 1 hour later although several time periods can be used. Untreated animals collapsed when exposed to the histamine aerosol. In these operations, the animals were observed and collapse times were recorded. The collapse times observed were then compared statistically with control animals treated with water alone with the control group usually being a long-term cumulative control. When tested by the above procedure, the compounds of the present invention were found to produce a bronchodilating effect.

The compounds of the present invention are conveniently prepared by the reaction of a 6-halo-7,8,9,10-tetrahydro-1,2,4-triazolo[3,4-a]phthalazine with an appropriate amine of the formula

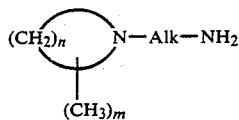

where Alk, m and n are defined as above. The 6-halo substituent is preferably chlorine although it can also be bromine. This 6-halo compound is reacted with an excess of the amine in an inert solvent medium. More specifically, the reaction is carried out at the boiling temperature under reflux. The solvent medium can actually be an excess of the amine used in the reaction or an inert organic solvent such as 2-methoxyethanol. The product is recovered by conventional procedures such as concentration under reduced pressure or by pouring the reaction mixture into ice water. The process usually gives the product as the free amine and this can be converted to the acid addition salts by standard procedures, e.g., dissolving the amine in ethanol and adding the anhydrous acid, whereupon the salt precipitates out.

The following examples are presented to illustrate the present invention but they should not be construed as limiting it in any way.

EXAMPLE 1

A solution of 5.0 g of 6-chloro-7,8,9,10-tetrahydro-1,2,4-triazolo[3,4-a]phthalazine and 10.0 g of 1-(2-aminoethyl)pyrrolidine in 50 ml of 2-methoxyethanol was heated at reflux for 15 hours. The solution was then concentrated and the resulting residue was partitioned between methylene chloride and saturated aqueous sodium bicarbonate solution. The organic layer was separated, dried over sodium sulfate and concentrated. The concentrate was triturated with ether and the solid which formed was separated by filtration to give 6-[2-(1-pyrrolidinyl)ethylamino]-7,8,9,10-tetrahydro-1,2,4-triazolo[3,4-a]phthalazine melting at about 160°–162° C. after recrystallization from a mixture of toluene and hexane. This compound has the following structural formula

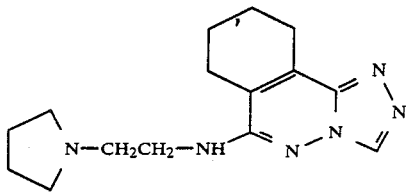

EXAMPLE 2

An ethanol solution of 6-[2-(1-pyrrolidinyl)ethylamino]-7,8,9,10-tetrahydro-1,2,4-triazolo[3,4-a]phthalazine was treated with an excess of ethereal hydrogen chloride. The precipitate which formed was separated by filtration to give 6-[2-(1-pyrrolidinyl)ethylamino]-7,8,9,10-tetrahydro-1,2,4-triazolo[3,4-a]phthalazine dihydrochloride melting at about 274°–275° C.

A solution of 20.0 g of 6-[2-(1-pyrrolidinyl)ethylamino]-7,8,9,10-tetrahydro-1,2,4-triazolo[3,4-a]phthalazine in 60 ml of 2-propanol was heated to reflux and 6 ml of concentrated hydrochloric acid was added slowly. An exothermic reaction took place and a white precipitate formed immediately. The mixture was refluxed for 30 minutes and then cooled. The solid was separated by filtration, washed thoroughly with 2-propanol and then dried at 50° C. under reduced pressure to give 6-[2-(1-pyrrolidinyl)ethylamino]-7,8,9,10-tetrahydro-1,2,4-triazolo[3,4-a]phthalazine hydrochloride hydrate.

To a refluxing solution of 15.0 g of 6-[2-(1-pyrrolidinyl)ethylamino]-7,8,9,10-tetrahydro-1,2,4-triazolo[3,4-a]phthalazine in 45 ml of ethanol was slowly added a solution of 13.2 g of phosphoric acid in an equal volume of ethanol. An exothermic reaction with vigorous foaming took place. The resulting slurry was refluxed for 1 hour and then cooled. The solid was separated by filtration, washed with ethanol and with absolute ethanol, and then dried at 50° C. under reduced pressure to give 6-[2-(1-pyrrolidinyl)ethylamino]-7,8,9,10-tetrahydro-1,2,4-triazolo[3,4-a]phthalazine diphosphate.

A solution of 522.5 g of 6-[2-(1-pyrrolidinyl)ethylamino]-7,8,9,10-tetrahydro-1,2,4-triazolo[3,4-a]phthalazine in 2 liters of ethanol was heated to 60° C. and filtered. The filtrate was diluted with 1 additional liter of ethanol and then heated close to reflux temperature. A mixture of 500 ml of ethanol and 207 g of 85.3% phosphoric acid was then slowly dripped into the solution of the amine. A solid crystallized out to give a thick slurry. The slurry was refluxed for 6 hours and then cooled to room temperature and filtered. The separated solid was washed twice with ethanol and then vacuum dried for 16 hours in an oven at 50° C. to give 6-[2-(1-pyrrolidinyl)ethylamino]-7,8,9,10-tetrahydro-1,2,4-triazolo[3,4-a]phthalazine monophosphate.

EXAMPLE 3

The procedure of Example 1 was repeated using 6-chloro-7,8,9,10-tetrahydro-1,2,4-triazolo[3,4-a]phthalazine and the appropriate amine. The product obtained was then reacted with hydrogen chloride according to the procedure described in the first paragraph of Example 2 to give the corresponding salt. In this way, the following compounds were obtained:

6-[2-(1-Piperidinyl)ethylamino]-7,8,9,10-tetrahydro-1,2,4-triazolo[3,4-a]phthalazine melting at about 182°–183° C. after recrystallization from a mixture of toluene and hexane.

6-[2-(1-Piperidinyl)ethylamino]-7,8,9,10-tetrahydro-1,2,4-triazolo[3,4-a]phthalazine dihydrochloride melting at greater than 280° C.

6-[2-(2-Methyl-1-pyrrolidinyl)ethylamino]-7,8,9,10-tetrahydro-1,2,4-triazolo[3,4-a]phthalazine melting at about 139°–140° C.

6-[2-(2-Methyl-1-pyrrolidinyl)ethylamino]-7,8,9,10-tetrahydro-1,2,4-triazolo[3,4-a]phthalazine dihydrochloride dihydrate melting at about 254°–256° C.

EXAMPLE 4

A solution of 5.0 g of 6-chloro-7,8,9,10-tetrahydro-1,2,4-triazolo[3,4-a]phthalazine in 25 ml of 1-(2-aminoethyl)-4-methylpiperidine was heated at reflux for 15 hours and then poured into ice water. The resulting off-white solid was separated by filtration and recrystallized from toluene to give 6-[2-(4-methyl-1-piperidinyl)ethylamino]-7,8,9,10-tetrahydro-1,2,4-triazolo[3,4-a]phthalazine melting at about 180°–181° C.

The amine obtained above was dissolved in methylene chloride and then treated with an excess of ethereal hydrogen chloride. The solid which formed was separated by filtration to give 6-[2-(4-methyl-1-piperidinyl)ethylamino]-7,8,9,10-tetrahydro-1,2,4-triazolo[3,4-a]phthalazine hydrochloride hemihydrate melting at greater than 285° C.

EXAMPLE 5

When the procedure of Example 4 was repeated using 1-(3-aminopropyl)-4-methylpiperidine in place of the 1-(2-aminoethyl)-4-methylpiperidine, the following compounds were obtained:

6-[3-(4-Methyl-1-piperidinyl)propylamino]-7,8,9,10-tetrahydro-1,2,4-triazolo[3,4-a]phthalazine melting at about 173°–174° C.

6-[3-(4-Methyl-1-piperidinyl)propylamino]-7,8,9,10-tetrahydro-1,2,4-triazolo[3,4-a]phthalazine dihydrochloride hemihydrate melting at about 269° C.

EXAMPLE 6

A solution of 10.0 g of 6-chloro-3-methyl-7,8,9,10-tetrahydro-1,2,4-triazolo[3,4-a]phthalazine and 12.8 g of 1-(2-aminoethyl)pyrrolidine in 50 ml of 2-methoxyethanol was heated at reflux for 15 hours. The reaction mixture was poured into 150 ml of cold water and the white precipitate which formed was separated by filtration and air dried to give 3-methyl-6-[2-(1-pyrrolidinyl)ethylamino]-7,8,9,10-tetrahydro-1,2,4-triazolo[3,4-a]phthalazine melting at about 184°–186° C.

EXAMPLE 7

A solution of 5.0 g of 6-chloro-7,8,9,10-tetrahydro-1,2,4-triazolo[3,4-a]phthalazine in 25 ml of 1-(3-aminopropyl)pyrrolidine was heated at reflux for 15 hours. Excess amine was removed by distillation and the resulting residue was partitioned between methylene chloride and saturated aqueous sodium bicarbonate solution. The organic layer was separated, dried over sodium sulfate and concentrated. The brown residue obtained was triturated with ether and the resulting solid was recrystallized from toluene to give 6-[3-(1-pyrrolidinyl)propylamino]-7,8,9,10-tetrahydro-1,2,4-triazolo[3,4-a]phthalazine melting at about 169°–171° C.

The amine obtained above was dissolved in ethanol and treated with an excess of ethereal hydrogen chloride. The solid which formed was separated by filtration to give 6-[3-(1-pyrrolidinyl)propylamino]-7,8,9,10-tetrahydro-1,2,4-triazolo[3,4-a]phthalazine dihydrochloride hemihydrate melting at about 277°–278° C.

EXAMPLE 8

When the procedure of Example 7 was repeated using 1-(3-aminopropyl)-2-methylpiperidine in place of the 1-(3-aminopropyl)pyrrolidine, the following compounds were obtained:

6-[3-(2-Methyl-1-piperidinyl)propylamino]-7,8,9,10-tetrahydro-1,2,4-triazolo[3,4-a]phthalazine melting at about 128°–129° C. after recrystallization of the original crude product from toluene.

6-[3-(2-Methyl-1-piperidinyl)propylamino]-7,8,9,10-tetrahydro-1,2,4-triazolo[3,4-a]phthalazine dihydrochloride hemihydrate melting at about 262°–265° C.

EXAMPLE 9

A solution of 9.1 g of 6-chloro-7,8,9,10-tetrahydro-1,2,4-triazolo[3,4-a]phthalazine and 17.7 g of 1-(4-aminobutyl)pyrrolidine in 50 ml of 2-methoxyethanol was heated at reflux for 16 hours. The reaction mixture was then poured into ice water and the tan solid which formed was separated by filtration and recrystallized from toluene to give 6-[4-(1-pyrrolidinyl)butylamino]-7,8,9,10-tetrahydro-1,2,4-triazolo[3,4-a]phthalazine melting at about 158.5°–160° C.

The amine obtained above was dissolved in methylene chloride and then treated with an excess of ethereal hydrogen chloride to give 6-[4-(1-pyrrolidinyl)butylamino]-7,8,9,10-tetrahydro-1,2,4-triazolo[3,4-a]phthalazine sesquihydrochloride melting at about 237°–238° C.

EXAMPLE 10

1-Chloro-4-hydrazino-5,6,7,8-tetrahydrophthalazine, also nameable as 3-chloro-4,5-tetramethylene-6-hydrazino pyridazine, (50 g, 0.25 mol) was mixed with 250 milliliters of formic acid. The mixture was heated at the boiling temperature under reflux for 2 hours. The mixture was concentrated by evaporation under reduced pressure, and the oily residue mixed with saturated aqueous sodium bicarbonate solution. The resulting white solid was separated by filtration, washed with water and dried in air. The 6-chloro-7,8,9,10-tetrahydro-1,2,4-triazolo[3,4-a]phthalazine product was recrystallized from alcohol-hexane and found to melt at 124°–125° C.

When the above procedure was repeated using acetic acid or propionic acid in place of formic acid, the products obtained were 6-chloro-3-methyl-7,8,9,10-tetrahydro-1,2,4-triazolo[3,4-a]phthalazine and 6-chloro-3-ethyl-7,8,9,10-tetrahydro-1,2,4-triazolo[3,4-a]phthalazine, respectively.

What is claimed is:

1. A compound of the formula

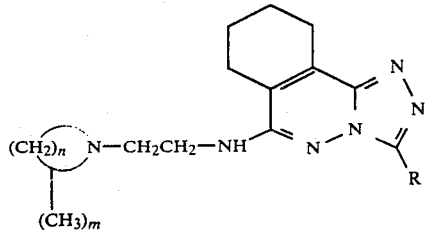

wherein R is hydrogen or alkyl of 1–4 carbon atoms; m is 0 or 1; and n is 4 or 5; and the pharmaceutically acceptable acid addition salts thereof.

2. A compound according to claim 1 which has the formula

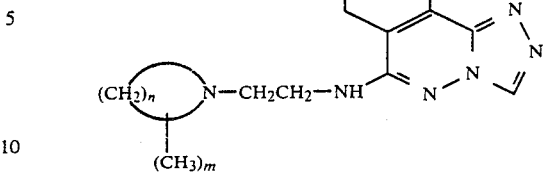

wherein m is 0 or 1 and n is 4 or 5; and the pharmaceutically acceptable acid addition salts thereof.

3. A compound according to claim 1 which is 6-[2-(1-pyrrolidinyl)ethylamino]-7,8,9,10-tetrahydro-1,2,4-triazolo[3,4-a]phthalazine and the pharmaceutically acceptable acid addition salts thereof.

4. A compound according to claim 1 which is 6-[2-(1-piperidinyl)ethylamino]-7,8,9,10-tetrahydro-1,2,4-triazolo[3,4-a]phthalazine.

5. A compound according to claim 1 which is 6-[2-(2-methyl-1-pyrrolidinyl)ethylamino]-7,8,9,10-tetrahydro-1,2,4-triazolo[3,4-a]phthalazine.

* * * * *